(12) United States Patent
Malcolm Albee et al.

(10) Patent No.: US 8,696,684 B2
(45) Date of Patent: Apr. 15, 2014

(54) ANIMAL TAG APPLICATOR

(75) Inventors: Joan Malcolm Albee, Bar Harbor, ME (US); Paul C. Sabin, Needham, MA (US); Douglas G. Sabin, Marblehead, MA (US); Terry Dale Walters, Gouldsboro, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 86 days.

(21) Appl. No.: 13/249,443

(22) Filed: Sep. 30, 2011

(65) Prior Publication Data

US 2012/0116414 A1    May 10, 2012

Related U.S. Application Data

(60) Provisional application No. 61/410,038, filed on Nov. 4, 2010.

(51) Int. Cl.
*A61B 17/00*    (2006.01)
*A61D 1/04*    (2006.01)

(52) U.S. Cl.
USPC ........................................................ 606/117

(58) Field of Classification Search
USPC ............ 606/117; 40/302; 140/93.4, 150–154
See application file for complete search history.

(56) References Cited

U.S. PATENT DOCUMENTS 3,550,647 A * 12/1970 Beach ........................ 140/93.4
2009/0223032 A1    9/2009 Luo et al.

* cited by examiner

*Primary Examiner* — Thomas McEvoy
(74) *Attorney, Agent, or Firm* — Alchemy-Partners, PC

(57) ABSTRACT

Described are an animal tag applicator, a device for advancing a strip of animal tags, a leg bending die for bending the legs of animal tags, and methods for applying an animal tag to a body part of an animal.

8 Claims, 9 Drawing Sheets

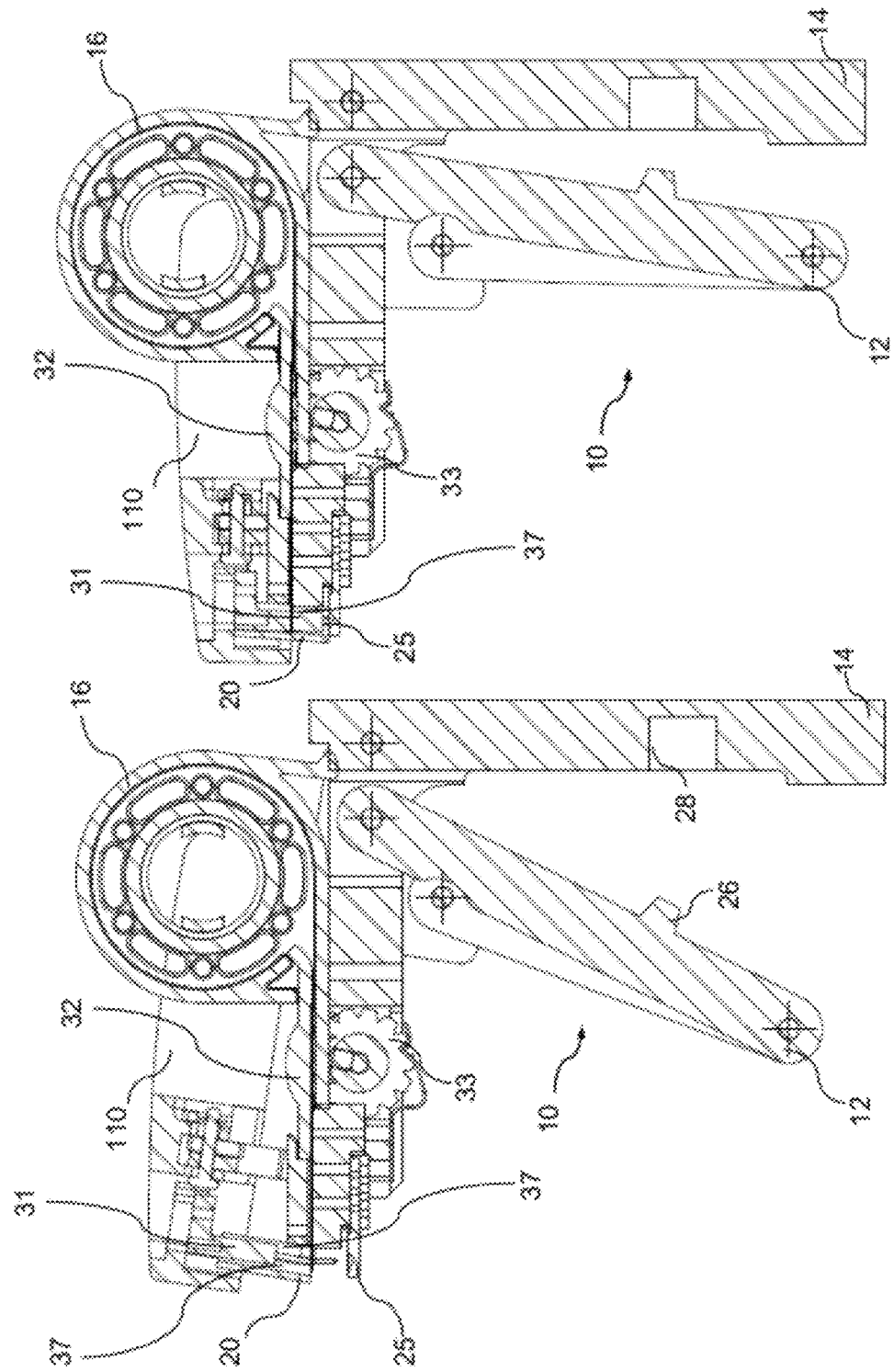

ANIMAL TAG APPLICATOR

CROSS REFERENCE TO RELATED DOCUMENTS

This application claims priority to provisional patent application No. 61/410,038 entitled "Mouse Tagger," filed Nov. 4, 2010, the entire disclosure of which is hereby incorporated by reference herein.

BACKGROUND

1. Field of the Invention

The present invention relates to an applicator for an ear tag and a method of applying an ear tag to an animal.

2. Related Art

Current pendant design ear identification tags for lab rodents and identification tags that clip around the ears of lab rodents have various problems. For example, such tags may tear out, the animal may get its claw caught under the side of the tag, the tag may catch on another object, etc.

SUMMARY

According to a first broad aspect of the present invention, there is provided a device comprising: an applicator frame for supporting a tag strip, a die frame for receiving a die assembly and moveable in a first vertical direction and a second vertical direction; a die assembly disposed and mounted within the die frame so that the die assembly is movable in the first vertical direction and the second vertical direction relative to the die frame, the die assembly comprising a first pincher and a second pincher that are rotatable in two opposite rotational directions with respect to each other; a die assembly stop for stopping movement of the die assembly in the first vertical direction when the die assembly reaches a stopped position, and an anvil disposed on the applicator frame configured to receive the tag strip thereon, the anvil configured to work cooperatively with the die assembly when the first pincher and second pincher rotate in the two opposite rotational direction with respect to each other to thereby manipulate tag legs extending outwardly from the tag strip.

According to a second broad aspect of the present invention, there is provided a method comprising the following steps: (a) supporting a tag strip comprising tags having outwardly extending tag legs and lying generally flat along at 0 degree reference plane on an anvil; (b) rotating a first pincher and a second pincher in opposite rotational directions to contact a pair of outwardly extending tag legs of one tag of the tag strip and bend the pair of tags on opposite sides of the anvil to thereby bend each leg of the pair of tag legs beyond 90 degrees relative to the reference plane.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

Still other aspects, features, and advantages of the present invention are readily apparent from the following detailed description, simply by illustrating a number of exemplary embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The accompanying drawings, which are incorporated herein and constitute part of this specification, illustrate exemplary embodiments of the invention and, together with the general description given above and the detailed description given below, serve to explain the features of the invention.

FIG. 3 is an interior side view of the applicator of FIG. 1 in an open handle position according to an exemplary disclosed embodiment;

FIG. 4 is an interior side view of the applicator of FIG. 1 in a closed handle position according to an exemplary disclosed embodiment;

DETAILED DESCRIPTION OF THE PREFERRED EMBODIMENTS

Definitions

Figure 1:
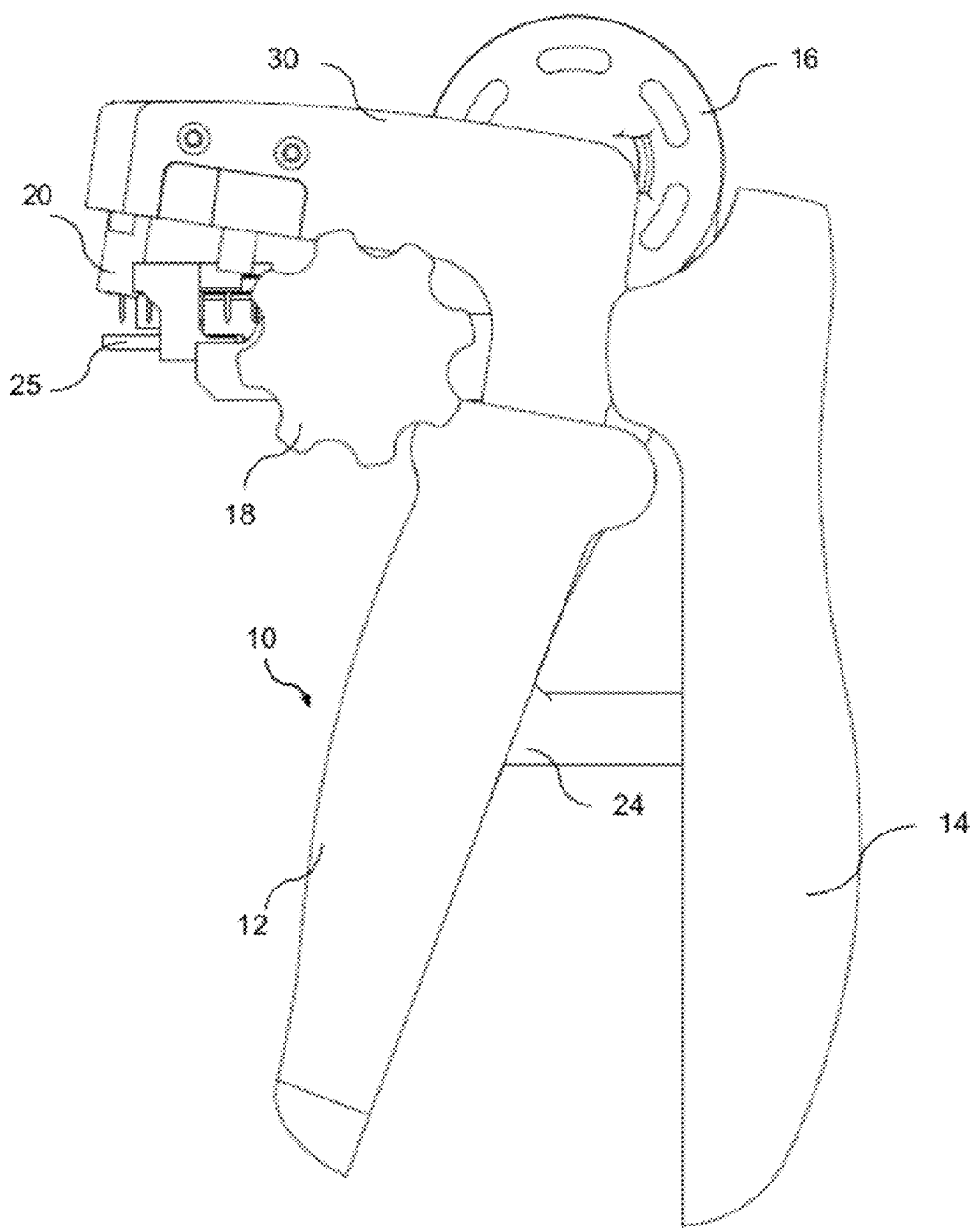
FIG. 1 is a schematic illustration of an animal tag applicator according to an exemplary disclosed embodiment.

Where the definition of a term departs from the commonly used meaning of the term, applicant intends to utilize the definitions provided below, unless specifically indicated.

For the purposes of the present invention, directional terms such as "top", "bottom", "upper", "lower", "above", "below", "left", "right", "horizontal", "vertical", "upward", "downward", etc., are merely used for convenience in describing the various embodiments of the present invention.

For the purposes of the present invention, the term "alpha-numeric" refers to identification codes including numbers and/or letters. Examples of alpha-numeric codes include: 132, ADB, 8A3, X24, etc.

For the purposes of the present invention, the term "animal tag" refers to any type of tag attached to an animal. One example of an animal tag is an "ear tag", which is an animal tag designed to be attached to an ear of an animal.

For the purposes of the present invention, the term "distal end" refers to the free end of a leg and the end of an animal tag applicator and the end of each of the components of the actuator that is held away from the user when the animal tag applicator is in use.

For the purposes of the present invention, the term "final vertical bend" and "finally vertically bent" refer to further bending partially vertically bent legs of an animal tag to a vertical position where legs of the tags may be inserted through the ear or other body part of an animal.

For the purposes of the present invention, the term "full squeeze" refers to a squeeze and release of a squeezable handle of a tag applicator of the present invention that is sufficient to cause a tag strip to advance by one location. The amount of force that is required for a full squeeze may be dependent on several factors, including the spring force of the spring that biases apart the handle members of a squeezable handle of the present invention. The term "full squeeze" may also refer to a squeeze and release of a squeezable handle of a tag applicator of the present invention, wherein, in some disclosed embodiments, the tag strip is manually advanced independent of the squeezable handle.

For the purposes of the present invention, the term "identification code" refers to a code that identifies an animal to which an animal tag of the present invention has been attached. The identification code may also include various information about the animal in addition to a code that uniquely identifies the animal. For example, the identification code may include information about the date the animal was tagged, the parentage of the animal, the experiment being conducted on the animal, etc.

For the purposes of the present invention, the term "partial squeeze" refers to a squeeze and release of a squeezable handle of a tag applicator of the present invention that is not sufficient to cause a tag strip to advance by one location. The term "partial squeeze" may also refer to a squeeze and release of a squeezable handle of a tag applicator of the present invention, wherein, in some disclosed embodiments, the tag strip is manually advanced independent of the squeezable handle For the purposes of the present invention, the term "proximal end" refers to the end of a leg that joins the plaque to which the leg is joined and to the end of an animal tag applicator and the end of each of the components of the actuator that is closest to the user when the animal tag applicator is in use.

For the purposes of the present invention, the term "sequential set of animal tags" refers to animal tags that are arranged in a tag strip of animal tags so that the respective codes of the animal tags form a sequence. The codes of the animal tags may be human-readable and/or machine-readable. In some disclosed embodiments of the invention, the animal tags may be non-sequential.

For the purposes of the present invention, the term "unibody construction" or "unibody" refers to an animal tag or tag strip made from a single piece of material, such as the tag strips described below and shown in the drawings.

For the purposes of the present invention, the term "frangible" refers to any type of breakable connection between two items, such as two animal tags. For example, if two adjacent animal tags are formed from a single piece of material, the frangible connection may be a weakened piece of material between the animal tags that may be preferentially broken to allow the two or more animal tags to be separated. The material may be weakened by perforation, engraving, indentation, thinning, etc. Alternatively, the frangible connection may be a dry adhesive between two animal tags that is preferentially broken to separate the animal tags from each other in a manner that is similar to the way staples are separated from each other.

For the purposes of the present invention, the term "human-readable" refers to indicia that may be understood by a human. Human-readable indicia may take the form of letters, numbers, symbols, shapes, colors, etc., or any combination thereof Human-readable indicia generally comprise indicia that are understandable by a human. Such human-readable indicia may also correspond to or be translatable into a particular number or letter, or any combination of numbers and/or letters that may be interpreted by a human. For example, the sequential combination of a blue triangle, red square and yellow circle could stand for the alpha-numeric code 12A, with the blue triangle standing for 1, the red square for 2 and the yellow circle for A. Human-readable indicia may be read by a human using the naked eye, or, usually, given the size of the indicia of the invention, with the aid of one or more optical magnifying lenses, a still camera, a movie camera, a video-recorder, etc. that may be used to aid a human in reading the visible indicia.

For the purposes of the present invention, the term "indicia" refers to markings on the plaque of a tag of the present invention. Indicia may be combinations of letters and/or numbers, and/or symbols and/or colors and/or shapes and/or codes, etc. Indicia may be "human-readable" and/or "machine-readable."

For the purposes of the present invention, the term "length" with respect to a plaque with legs extending from only two sides of the plaque refers the distance across a plaque in the direction parallel to which the legs extend from the plaque. For a plaque with legs extending from more than two sides and for a circular plaque, the term "length" refers to the longest dimension of the plaque aligned in parallel with at least one leg. With respect to legs, the term "length" refers to the longest dimension of a leg.

For the purposes of the present invention, the term "machine-readable code" refers to code that is readable by a machine, such as a scanner, computer, PDA, cell phone, etc. Machine-readable indicia are one type of a machine-readable code, but human-readable code may be stored in a device, such as an RFID tag, that is mounted on or mounted in an animal tag.

For the purposes of the present invention, the term "machine-readable indicia" refers to indicia that are readable by a machine such as a scanner, computer, PDA, cell phone, etc. Examples of machine-readable indicia include one-dimensional bar codes, 2D bar codes, matrix codes, etc. Some machine-readable indicia may also be human-readable. For example, numbers, letters, colors, symbols, etc. may be both human-readable and machine-readable.

For the purposes of the present invention, the term "maximum diameter" with respect to a plaque refers to the longest line across the plaque, including diagonal lines. The maximum diameter of a rectangular plaque corresponds to a diagonal distance between two opposite corners of the plaque. For example, for a square plaque that has a width and length of 5 mm, the maximum diameter will be 7.07 mm, i.e., about 7.1 mm.

For the purposes of the present invention, the term "partial vertical bend" and "partially vertically bent" refers to a bending of the legs of an animal tag in a vertical direction that is performed before a final vertical bending operation. Although in the embodiments of the present invention shown in the drawings and described below there is one partial vertical bending operation performed on each tag, the present invention contemplates that it may be desirable in some instances to perform multiple partial vertical bending operations prior to a final bending operation on an animal tag. Such partial bending operations may be performed using multiple partial vertical bending dies in a single leg bending die or additional partial vertical bending dies in additional leg bending dies.

For the purposes of the present invention, the term "preferential bending region" refers to a portion of a leg of the present invention that is thinned, flattened, weakened, etc. so that when pressure is applied to the end of the leg, the leg will preferentially bend in this region.

For the purposes of the present invention, the term "thickness" for a plaque refers to the dimension of the plaque perpendicular to the upper and lower surfaces of the plaque. The term "thickness" for a leg refers to the dimension of the leg perpendicular to the upper and lower surfaces of the plaque.

For the purposes of the present invention, the term "unibody construction" refers to a component that is made from a single piece of material. For example, in one embodiment of the present invention, a leg bending die and a shearing die may be part of a unibody die piece.

For the purposes of the present invention, the term "width" with respect to a plaque refers to the dimension that is perpendicular to the length of the plaque in the plane of the upper or lower surface of the plaque. For the purposes of the present invention, with respect to a leg, the term "width" refers to a dimension of the leg perpendicular to the length of the leg and co-planar with either the upper or lower surface of the plaque.

Description

The present invention relates to an applicator for animal tags and methods of applying an animal tag of the type described in U.S. patent application Ser. No. 12/556,896, entitled "Lab Animal Ear Tag", to Albee et al., filed Sep. 10, 2009, and the entire contents and disclosure of this application are incorporated herein by reference. The plaque of the animal tag that is applied by the applicator is designed to be substantially flat and immobilized when secured to an animal. This prevents the animal tag from catching on anything in the animal's external environment, such as the wires of the cage in which the animal is kept. The animal also tends to ignore a small, flat and immobilized tag during grooming. It is important that the animal tag have a small size and weight to prevent detachment from or irritation of the ear of the animal.

When the animal tag is an ear tag, the ear tag is designed so that the ear of the animal is not crushed between the tag body and the legs as a result of the application of the animal tag to the ear by the applicator. In one embodiment, the plaque of the ear tag may be applied by the applicator so that the plaque is oriented on the animal's ear at right angles to the major access of elongation of the ear during growth of the animal, thereby allowing the tag to be applied to the ears of young animals and left attached for an extensive period of time (perhaps over the entire life of the animal) without tearing the ear or causing the ear to loop out away from the surface of the plaque.

Figure 2:
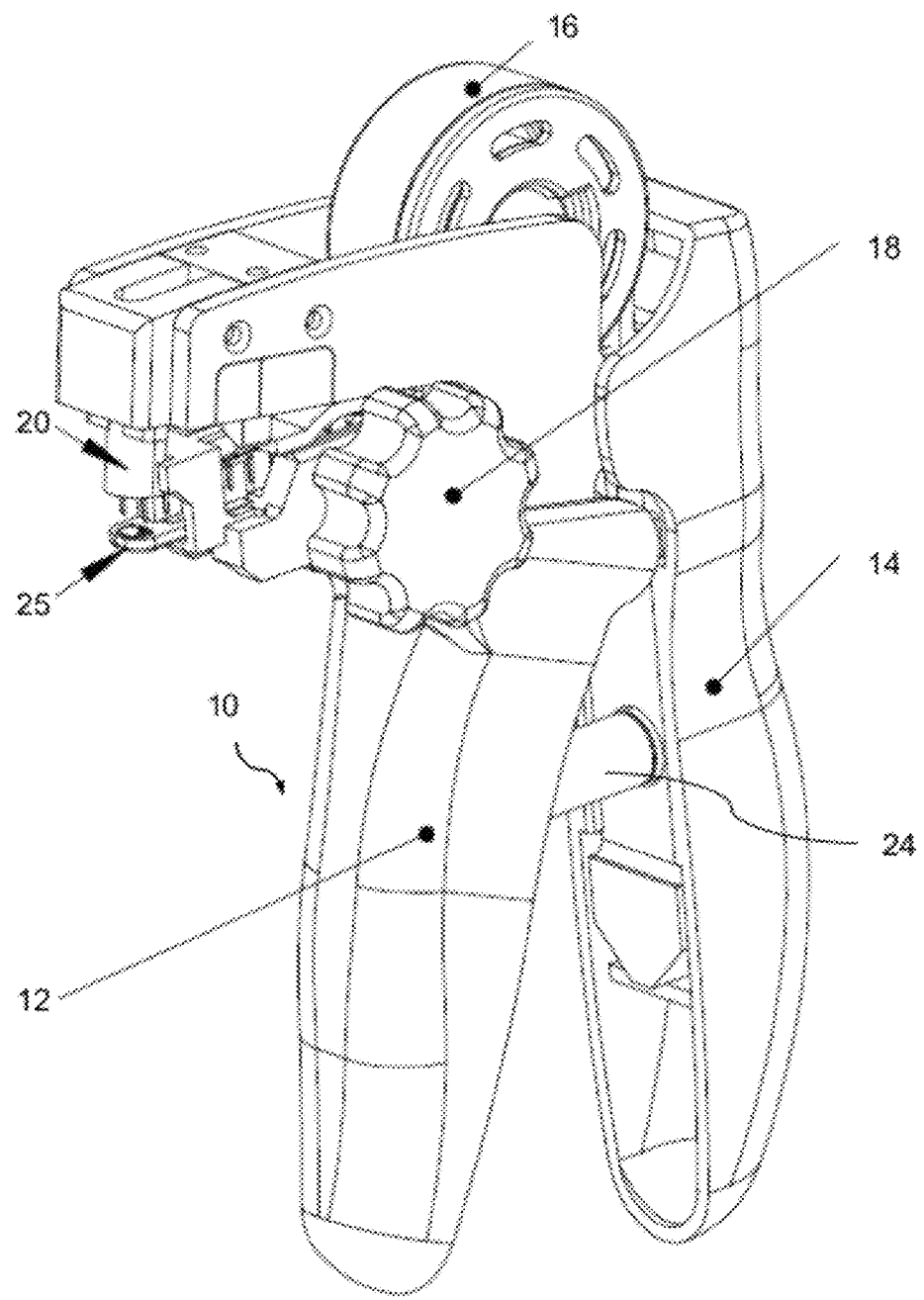
FIG. 2 is perspective view of the applicator of FIG. 1 according to an exemplary disclosed embodiment.

FIGS. 1 and 2 show an animal tag applicator 10 of the present invention having a handle comprising a front handle portion 12 and back handle portion 14. The front handle portion 12 acts as a pivotable handle member with respect to the back handle portion 14. The back handle portion 14 is considered as a stationary handle member. A handle spring 24 is disposed between the front handle portion 12 and the back handle portion 14. In some preferred embodiments, the handle spring 24 connects front handle portion 12 to back handle portion 14 and biases front handle portion 12 away from back handle portion 14. The handle spring 24 may be mounted between front handle portion 12 and back handle portion 14 by any means suitable for securing the handle spring 24 therebetween.

In one embodiment, turning to FIG. 3, an interior view of the applicator 10 is shown. Components of the front handle portion 12 may include a protruding portion 26 for engaging a first end of the handle spring 24. A recessed portion 28 may be disposed in a suitable location of the back handle portion 14 to receive the other end of the spring and thereby retaining the handle spring 24 (shown in FIG. 2) in a fixed location between the front handle portion 12 and the back handle portion 14.

The front handle portion 12 and the back handle portion 14 may work cooperatively during operation to actuate movement of the applicator 10. In a disclosed embodiment, front handle portion 12 is coupled to actuator 110. Both the front handle portion 12 and the back handle portion 14 may be securely attached to framework 30 (shown in FIG. 1). As front handle portion 12 pivots with respect to the back handle portion 14, actuator 110 is enabled to drive a tag from a tag cartridge as described below. Tag cartridge 16 is preferably situated in engagement within the framework 30 of the applicator 10. In one disclosed embodiment, the cartridge 16 includes an extended portion 32 for guiding a tag strip into engagement with a gearing mechanism 33 of the applicator 10. As demonstrated in FIGS. 3 and 4, the gearing mechanism 33 is sufficiently designed to mate with the tag strip received from the tag cartridge 16. When the gearing mechanism 33 is advanced, it urges the tag strip forwardly from the tag cartridge 16 in advancement towards tag guide 20. The gearing mechanism 33 may be mechanically coupled, for example to indexing knob 18 (FIGS. 1 and 2) to advance the tag strip.

As actuator 110 is driven downwardly, a shearing die 31 is driven downwardly to shear a shearable animal tag from a tag strip emanating from tag cartridge 16. Shearing die 31 continues to drive the shearable animal tag downwardly through a guide pathway 37 that extends through a guide portion of tag guide 20 so that legs of the sheared shearable animal tag are inserted through animal ear. In a disclosed embodiment, after the legs have been inserted through the animal ear, the legs of the sheared shearable animal tag may be bent under a plaque of the sheared shearable animal tag by leg forming die 25 to secure the applied the shearable animal tag to the animal ear. Additionally, leg forming die 25 may be employed to shear the legs of the tag such as prior to bending of the legs.

Figures 5, 6, 7:
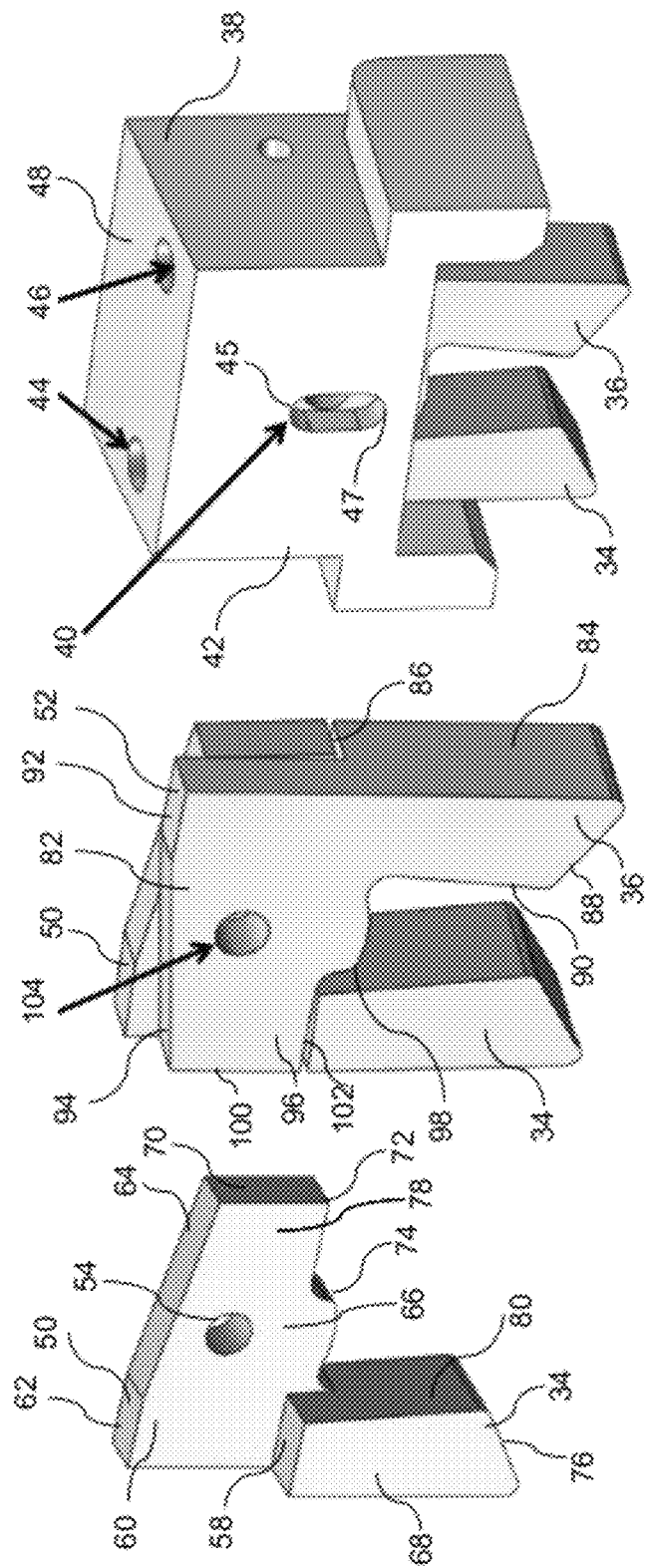
FIG. 5 is a perspective view of a pincher element according to an exemplary disclosed embodiment.
FIG. 6 is a perspective view of pincher elements in mated relation according to an exemplary disclosed embodiment.
FIG. 7 is a perspective view of the pincher elements of FIG. 6 disposed within a pincher frame according to an exemplary disclosed embodiment.

FIGS. 5-12 illustrate the bending mechanism of the applicator 10 for securing the tags. Turning to FIG. 7, embodiments of the disclosed invention provide a combination of rotating pinchers 34, 36 operatively and movably connected within a pincher frame 38. Rotating pinchers 34, 36 act as bending dies employed to manipulate tag legs of the disclosed tag. Pincher frame 38 preferably includes a pincher pivot pin slot 40 on a forward face 42 thereof A plurality of holes 44, 46 are fabricated within a top face 48 of pincher frame 38. The plurality of holes 44, 46 may receive adjustment set screws (not shown) for urging against a corresponding top contact surface 50, 52 of each respective rotating pincher 34, 36. While set screws are described in the present embodiment, any suitable means for adjusting the top contact surface 50, 52 may be utilized including hand manipulation. In a disclosed embodiment, the pincher frame 38 is made from aluminum material. The aluminum material is generally regarded as lightweight and employable in the disclosed application. Other suitable materials, such as stainless steel materials, however, may be employed which is sufficient for securing and enabling the pinchers 34, 36 as disclosed herein.

Turning to FIGS. 5 and 6, a first rotating pincher 34 and a second rotating pincher 36 are provided to cooperatively mate with one another in a final assembly. In a disclosed embodiment, the first rotating pincher 34 may be regarded as a reward pincher and the second rotating pincher 36 may be regarded as a forward pincher relative to one another in an assembled state. The first rotating pincher 34 and the second rotating pincher 36 may comprise any suitable materials for disclosed applications of bending and securing tag legs to an animal Some disclosed embodiments include aluminum for the first and second rotating pinchers 34, 36. The first rotating pincher 34 comprises a main body portion 66 having a pincher pivot pin hole 54. The first rotating pincher 34 is not only suitable configured to mate with the second rotating pincher 36, but is also designed to operatively rotate in cooperation with the applicator 10 and function to manipulate and secure a tag. As shown in FIG. 5, a first pincher leg portion 68 extends downwardly from the main body portion 66 of the first rotating pincher 34. A resting ledge 58 extends outwardly from an abutment surface 60 of the main body portion 66 and is integral with the first pincher leg portion 68. The first pincher leg portion 68 may include an outwardly extending angled bottom portion 76. An inner surface 80 of the first pincher leg portion 68 may be utilized as the working surface for bending tag legs as described below.

The main body portion 66 of first rotating pincher 34 preferably comprises a top surface 62. The top surface 62 is formed by a relatively flat top contact surface 50 which traverses into a downwardly decreasing angled top surface 64. The main body portion 66 extends into a projected member 78 which is formed by the angled top surface 64, bottom surface 74 and terminates at end 70. A portion 72 of bottom surface 74 is preferably configured to cooperatively lie in on a resting ledge 86 of the second rotating pincher 36 in an assembled fashion as shown in FIG. 6.

Turning to FIG. 6, the second rotating pincher 36 comprises a main body portion 66 having a pincher pivot pin hole 104. The second rotating pincher 36 is not only suitablely configured to mate with the first rotating pincher 34, but is also designed to operatively rotate in cooperation with the applicator 10 and function to manipulate and secure a tag. A second pincher leg portion 84 extends downwardly from the main body portion 82 of the second rotating pincher 36. In a similar configuration as the first rotating pincher 34, a resting ledge 86 of the second rotating pincher 36 extends outwardly from an abutment surface (not shown) of the main body portion 82 and is integral with the second pincher leg portion 36. The second pincher leg portion 84 may include an outwardly extending angled bottom portion 88. An inner surface 90 of the second pincher leg portion 84 may be utilized as the working surface for bending tag legs as described below. Together first rotating pincher 34 and second rotating pincher 36 form a U-shaped die assembly.

The main body portion 82 of second rotating pincher 36 preferably comprises a top surface 92. The top surface 92 is formed by a relatively flat top contact surface 52 which traverses into a downwardly decreasing angled top surface 94. The main body portion 82 extends into a projected member 96 which is formed by the angled top surface 94, bottom surface 98 and terminates at end 100. A portion 102 of bottom surface 98 is preferably configured to cooperatively lie on the resting ledge 58 of the first rotating pincher 34 in assembled fashion as shown.

A retaining pin or pincher pivot pin (not shown) may be inserted into the pincher pivot pin holes 54, 104 to retain the first and second rotating pinchers 34, 36 in abutment to one another. Each of the first and second rotating pinchers 34, 36 may rotate with respect to each other around the retaining pin. When the assembled first and second rotating pinchers 34, 36 are inserted within an interior of the pincher frame 38 (e.g., see FIG. 7), the pivot pin may be inserted into the pin slot 40 and through the pivot pin holes 54, 104 of first and second pinchers 34, 36. The pincher pivot pin slot 40 allows the inserted retaining pin to move up and down therein. As the pin moves up and down, the first and second rotating pinchers 34, 36 are allowed to move up and down to a degree relative to the pincher frame 38. The upper most limit 45 of the pincher pivot pin slot 40 will prevent the pin from moving upward. In a rested or what may be considered a free position, the inserted pin may be situated along the bottom of pivot pin slot 40 as it retains first and second pinchers 34, 36 in place and in an assembled stated within pincher frame 38. An interior of pincher frame 38 is sufficiently sized to receive the die assembly of pinchers 34, 36 to provide enough clearance to facilitate rotation and vertical movement of the pinchers 34, 36 within its receiving cavity.

Figure 8:
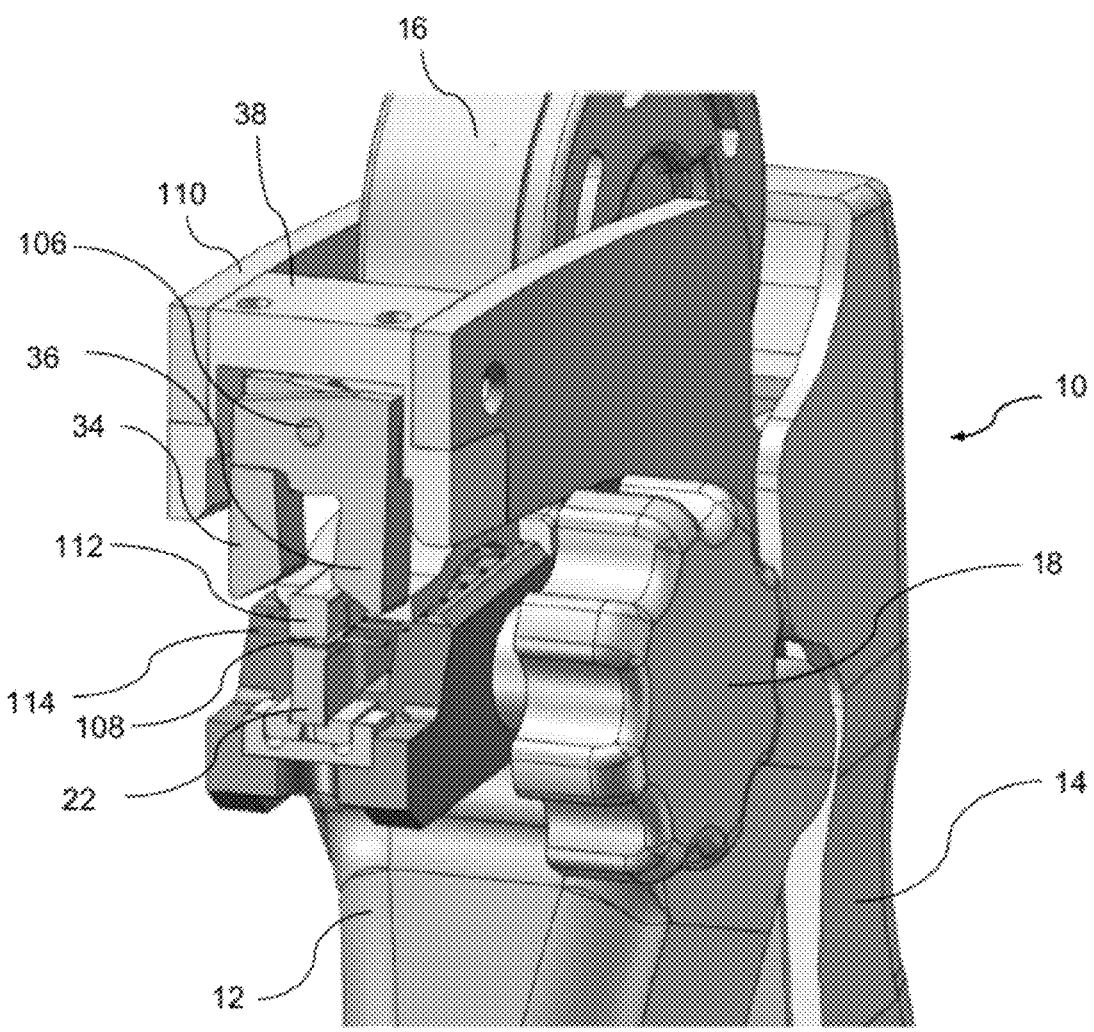
FIG. 8 is a cut-away view of the pincher assembly and pincher frame of FIG. 7 mounted to the applicator of FIG. 1 in a starting position according to an exemplary disclosed embodiment.

Turning to FIG. 8, the pincher frame 38 is shown mounted to the frame actuator 110 of applicator 10. A cut-away view of the pincher frame 38 shows the first and second rotating pinchers 34, 36 mounted therein via retaining pin or pincher pivot pin 106. The frame actuator 110 may be directly coupled to the front handle portion 12 (see also, FIG. 3). As the front handle portion 12 is urged toward the back handle portion 14, the actuator frame 110 is urged downwardly. As the actuator frame 110 is urged downwardly it brings the pincher frame 38 and first and second rotating pinchers 34, 36 towards the die assembly stop 112 and tag 108. In the illustrated starting position, i.e., when the front handle portion 12 and back handle portion 14 are in an open position, tag legs 114 of tag 108 are relatively flat, i.e., tag legs 114 lie generally flat at zero degrees in a horizontal reference plane. In this configuration, the pincher pivot pin 106 is located at the bottom 47 (FIG. 7) of the pincher pivot pin slot 40 in what is considered as a rested state or free position. The positioning of the pivot pin 106 at the bottom 47 is due to gravity.

Figure 9:
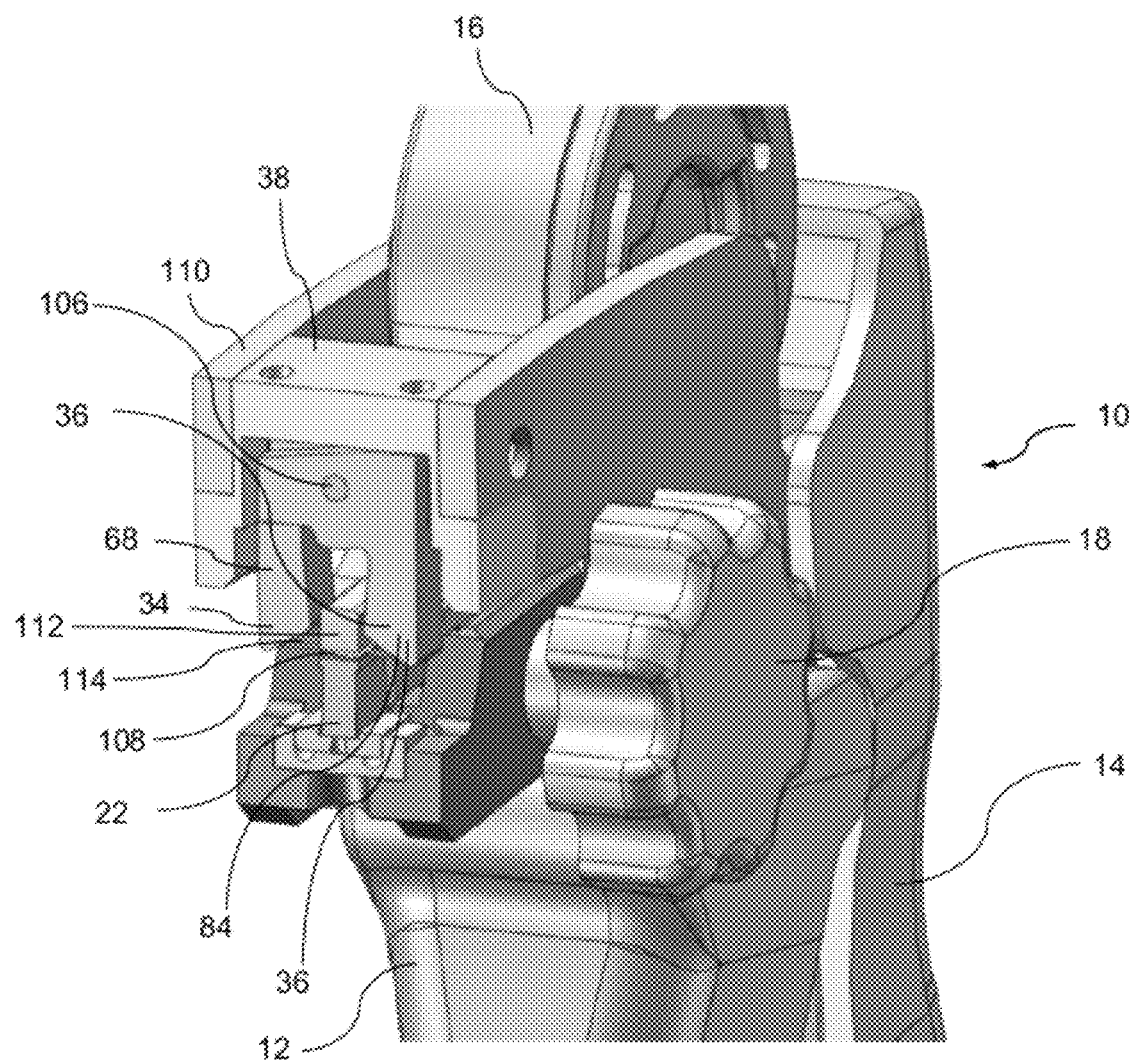
FIG. 9 is a cut-away view of the pincher assembly and pincher frame of FIG. 7 mounted to the applicator of FIG. 1 in an intermediate position according to an exemplary disclosed embodiment.

Turning to FIG. 9, an intermediate position of applicator 10 is illustrated showing a configuration of the front handle portion 12 relative to the back handle portion 14 as partially closed. The actuator frame 110 has been urged downwardly to bring the pincher frame 38 and first and second rotating pinchers 34, 36 closer towards the die assembly stop 112 and tag 108. It is noted that the tag 108 still remains flat at this point. The tag legs 114 may be in contact with the angled bottom portions 76, 88 of respective pincher legs 68 and 84. At this point, the tag legs 114 remain relatively flat or at zero degrees in a horizontal reference plane.

Figure 10:
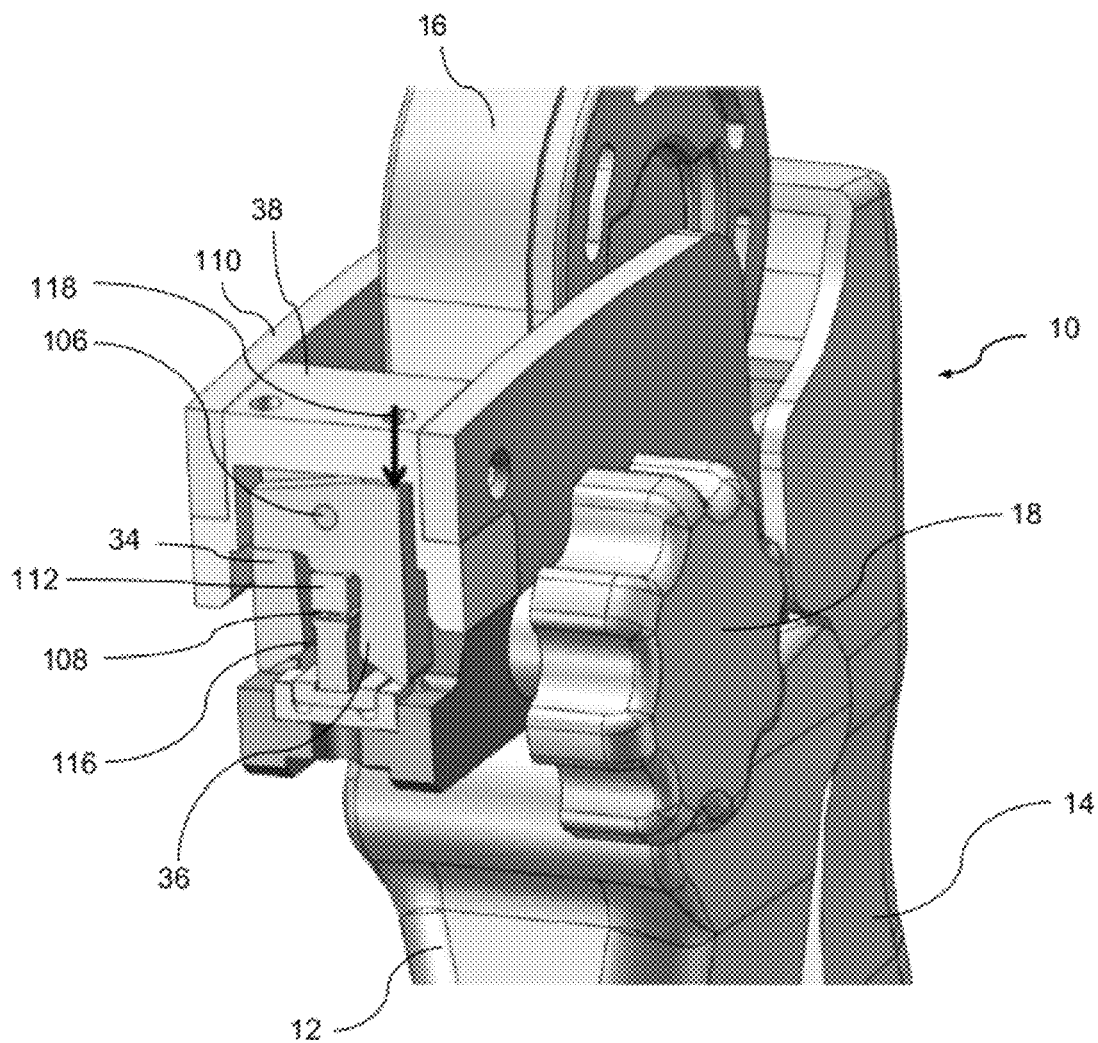
FIG. 10 is a cut-away view of the pincher assembly and pincher frame of FIG. 7 mounted to the applicator of FIG. 1 in a second intermediate position according to an exemplary disclosed embodiment.

In a another intermediate position, the front handle portion 12 relative to the back handle portion 14 is mostly closed. The second intermediate position may be considered a further advancement of the first intermediate position of the applicator 10. As shown in FIG. 10, pinchers 34, 36 are pushed down by the pincher frame 38 in a generally downward direction 118 to begin bending the legs 114 of tag 108. Bending occurs as the contact point 116 of each pincher 34, 36 engages tag legs 114 and along the inside surfaces 80, 90 (FIGS. 5 and 6) of pinchers 34, 36 The tag legs 114 are generally bent downwardly, but not quite at 90 degrees (from its original flat configuration within a zero degree reference plane) at the described intermediate position.

Figure 11:
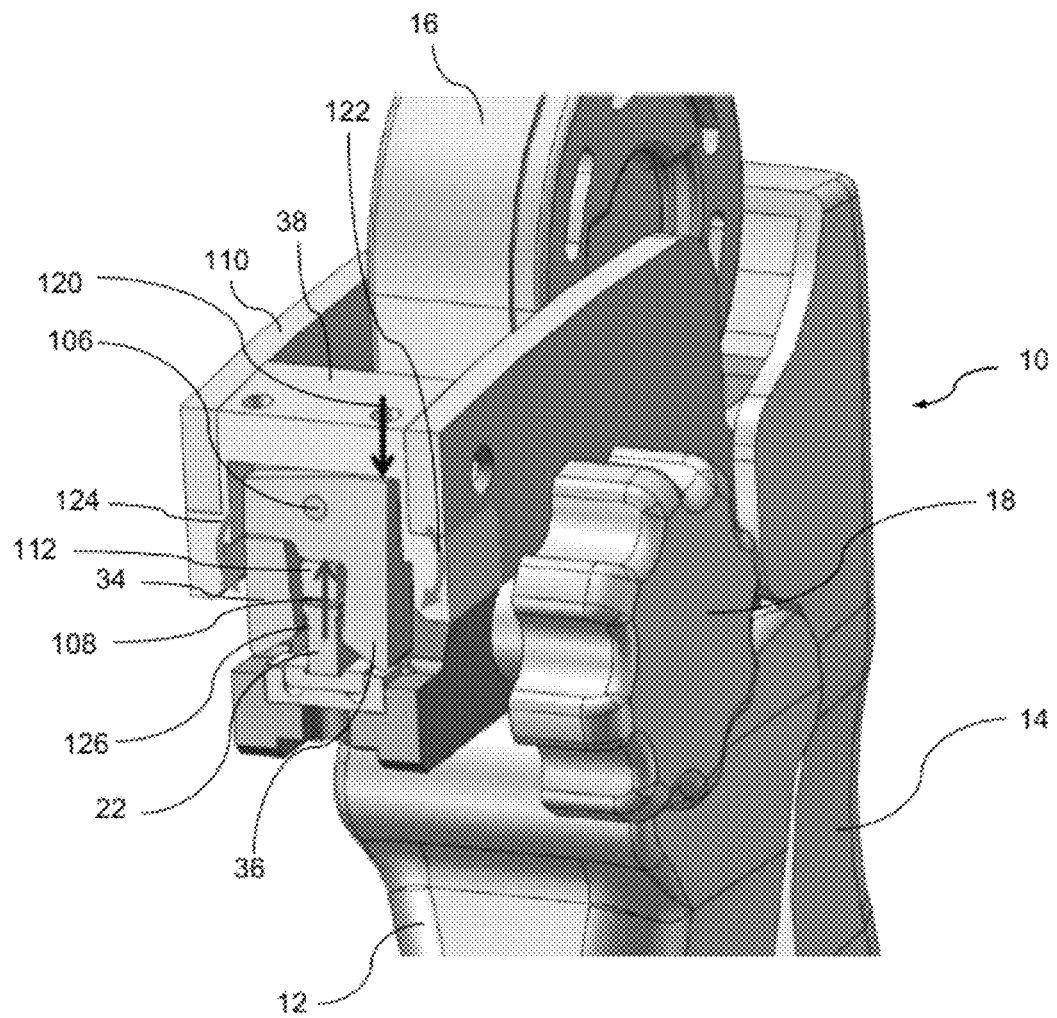
FIG. 11 is a cut-away view of the pincher assembly and pincher frame of FIG. 7 mounted to the applicator of FIG. 1 in an end position according to an exemplary disclosed embodiment.

FIG. 11 illustrates an end position of the handle portion 12 relative to the back handle portion 14. In the end position, the handle is in a fully closed position (e.g., see FIG. 4). The pinchers 34, 36 are pushed down by the pincher frame 38 in a generally downward direction 120 until the bottom surfaces 74, 98 (FIGS. 5 and 6) of the pinchers 34, 36 fully contact the top surface of die assembly stop 112. Die assembly stop 112 acts as a die assembly stop for stopping movement of the die assembly as it moves in a vertical direction. Thus in the disclosed embodiment, the die assembly stop 112 prevents further downward movement of pinchers 34, 36. The counteracting forces of the pincher frame 38 and the die assembly stop 112 cause the pincher pivot pin 106 to slide up in the pincher pivot pin slot 40 (not shown in FIG. 11). Due to the applied force of the pincher frame 38 to the top contact surfaces 50, 52 of the pinchers 34, 36 (FIGS. 5 and 6), each pincher 34, 36 rotates about retaining pin 106. The angled top surface 94 (FIG. 6) of pincher 36 allows pincher 36 to rotate about pincher pivot pin 106 inwardly in a clockwise direction 122. The angled top surface 64 (FIG. 5) of pincher 34 allows pincher 34 to rotate about pincher pivot pin 106 inwardly in a counter-clockwise direction 124. Thus, the tag legs 114 are generally bent by the inside surfaces 80, 90 (FIGS. 5 and 6) more than 90 degrees (from its original flat configuration within a zero degree reference plane) by rotating pinchers 34, 36. In some embodiments, the anvil 22 may be configured with an undercut 126 to facilitate the tag legs bending more than 90 degrees on each side of the anvil 22. Set screws 128, 130 (FIGS. 12A-12C) may be utilized for adjusting the control of finally bending the tag legs 114. The degree to which each of first and second rotating pinchers 34, 36 is able to rotate may also be based, in part, upon the angled configuration of the angled top surfaces 64, 94. Although set screws are shown as adjustors in the embodiment described above and shown in the drawings, other forms of adjustors may be used to set a position of the die assembly.

Figures 12A, 12B, 12C:
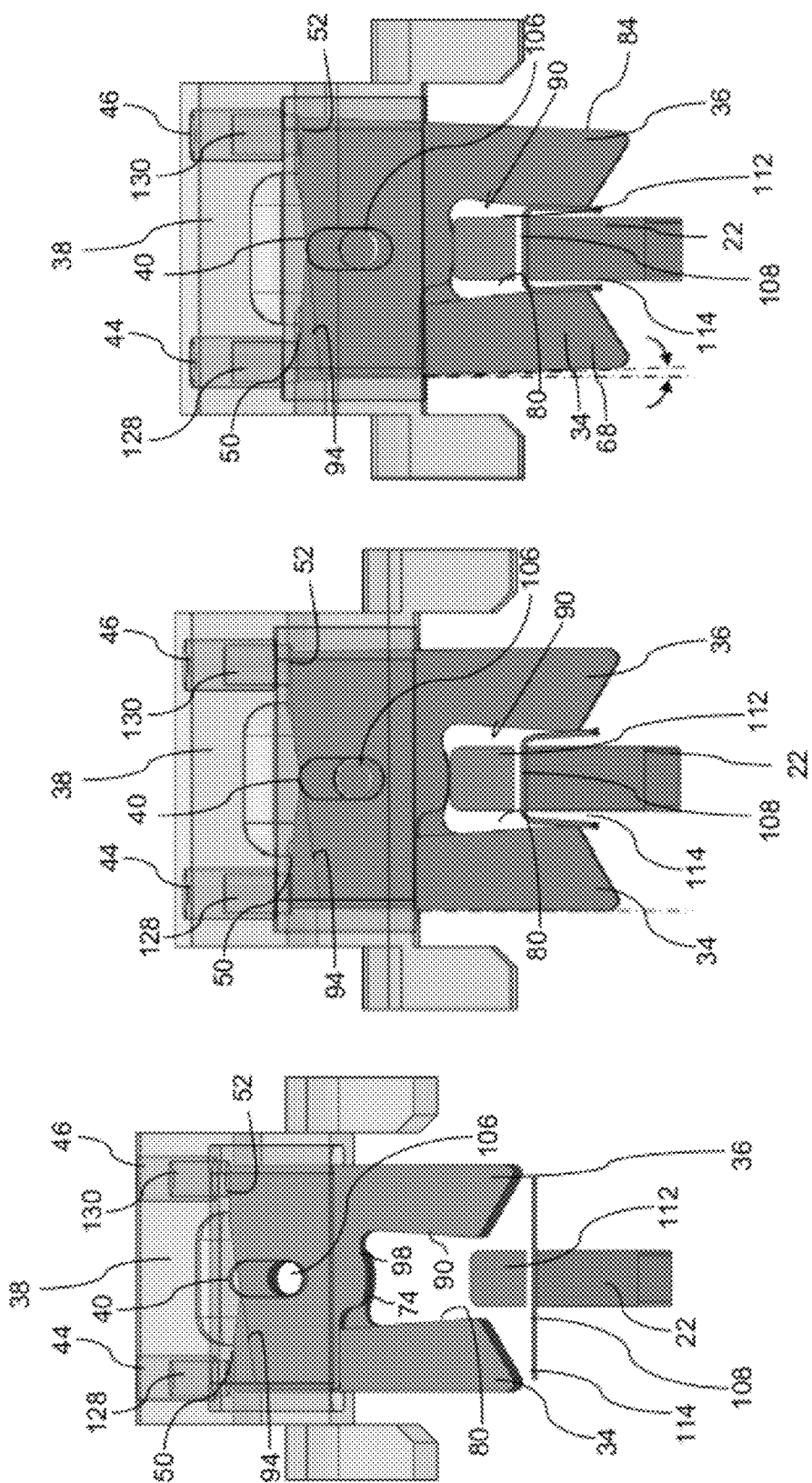
FIG. 12A illustrates a starting position of the pincher assembly and pincher frame in the treatment process of a tag element according to an exemplary disclosed embodiment.
FIG. 12B illustrates an intermediate position of the pincher assembly and pincher frame in the treatment process of a tag element according to an exemplary disclosed embodiment.
FIG. 12C illustrates an end position of the pincher assembly and pincher frame in the treatment process of a tag element according to an exemplary disclosed embodiment.

FIGS. 12A-12C illustrate various positions of the bending processes of the disclosed invention. In a starting position, i.e., when the handle is in a fully open position, FIG. 12A illustrates the pinchers 34, 36 positioned to engage tag legs 114 of tag 108. At this orientation, the two legs 114 lie generally flat at zero degrees in a horizontal reference plane. The pincher pivot pin 106 is configured to rest at the bottom of the pincher pivot pin slot 40 due to gravity. The set screws 128 and 130 are adjusted to provide a prescribed bending and rotation of pinchers 34, 36. In what may be considered as a resting position, the set screws 128, 130 may not be in direct engagement with the top contact surfaces 50, 52 of rotating pinchers 34, 36.

Turning to FIG. 12B, an intermediate position of the applicator 10 is illustrated showing the pinchers 34, 36 engaging the tag legs 114. The pincher frame 38 is actuated downwardly such that set screws 128, 130 engage top contact surfaces 50, 52 thereby urging contact point 116 of pinchers 34, 36 into engagement with tag legs 114 for initial bending. At this position, the tag legs 114 are bent not quite 90 degrees (from its original flat configuration within a zero degree reference plane) per side by pinchers 34, 36. As discussed, the downward movement of pincher frame 38 causes set screws 128 and 130 to make contact with contact surfaces 50, 52 of pinchers 34, 36. This, in turn, moves pinchers 34, 36 downwardly to cause the bottom surfaces 74, 94 of pinchers 34, 36 to come into contact with die assembly stop 112. The bottom surfaces 74, 94 of respective pinchers 34, 36 act as stop contacting surfaces of the die assembly for contacting the die assembly stop 112. The counteracting force of die assembly stop 112 may cause pincher pivot pin 106 to be urged upwardly into pincher pivot pin slot 40 in a generally vertical direction.

At a final position, wherein the handle is fully closed, FIG. 12C illustrates the pincher frame 38 in a final downward position and incapable of moving further due to the impedance of die assembly stop 112 acting against bottom surfaces 74, 94 of pinchers 34, 36. The continued pressure of the downward force of the pincher frame 38 acting against the upward force of the die assembly stop 112 may cause pincher pivot pin 106 to be urged further up pincher pivot pin slot 40. In addition, the applied force of the set screws 128 and 130 against the contact surfaces 50, 52 causes a rotation of pinchers 34, 36. The angled top surfaces 64, 94 are rotated upwardly within an interior of the pincher frame 38 thereby causing respective leg portions 68, 84 of pinchers 34, 36 to rotate inwardly. This rotational movement causes the legs 68, 84 to bend the tags 114 beyond 90 degrees (from its original flat configuration within a zero degree reference plane) on each side of tag 108.

In some embodiments of the present invention, each plaque of each animal tag has a X-dimension (the dimension aligned with the legs of an animal tag) of at least about 0.1450 inches and a Y-dimension (the dimension perpendicular to legs of an animal tag) of at least about 0.1050 inches. Each leg has an X-dimension of at least about 0.163 inches, a non-tapered portion X-dimension of at least about 0.142 and a Y dimension of at least about 0.018 inches. Each opening and indent has a Y-dimension of at least 0.006 inches. In one embodiment of the present invention, each plaque in a tag strip has an X-dimension of about 0.1470 inches and a Y-dimension of about 0.1070 inches, each leg has an X-dimension of about 0.168 inches, a non-tapered portion X-dimension of about 0.145 and a Y dimension of about 0.022 inches, and each opening and indent has a Y-dimension of about 0.010 inches. In some embodiments of the present invention, the animal tags may have a thickness of about 0.10 inches.

In some embodiments of the present invention, the opening and indents that form the tabs are a frangible connection that may be made by etching.

A tag strip of the present invention may be in the form of a roll having any number of animal tags. The number of animal tags in a tag strip is limited only by the size of the cartridge in which the tag strip is contained.

Various types of sequential indicia may be used on the animal tags of the strip, including human-readable indicia, machine-readable indicia such as one-dimensional and 2D bar codes, color-based indicia, symbol-based indicia, shape-based indicia, etc. Also, instead of visible indicia, a strip of sequential animal tags may include animal tags having machine-readable codes, such as RFID tags.

Also, although particular types of legs are shown in the drawing figures, a strip of animal tags of the present invention may have various types of leg configurations and types. Also, the legs may be shorter or longer in the X-dimension than the plaques in a strip of animal tags.

Metal animal tags and strips of animal tags of the present invention may be made from a metal sheet by well-known processes such as laser etching, metal stamping, etc.

While the present invention has been disclosed with references to certain embodiments, numerous modifications, alterations and changes to the described embodiments are possible without departing from the spirit and scope of the present invention, as defined in the appended claims. Accordingly, it is intended that the present invention not be limited to the described embodiments, but that it has the full scope defined by the language of the following claims, and equivalents thereof.

What is claimed is:

1. A device comprising:
   an applicator frame for supporting a tag strip,
   a die frame for receiving a die assembly and moveable in a first vertical direction and a second vertical direction;
   a die assembly disposed and mounted within the die frame so that the die assembly is movable in the first vertical direction and the second vertical direction relative to the die frame, the die assembly comprising a first pincher and a second pincher that are rotatable in two opposite rotational directions with respect to each other;
   a die assembly stop for stopping movement of the die assembly in the first vertical direction when the die assembly reaches a stopped position, and
   an anvil disposed on the applicator frame configured to receive the tag strip thereon, the anvil configured to work cooperatively with the die assembly when the first pincher and second pincher rotate in the two opposite rotational direction with respect to each other to thereby manipulate tag legs extending outwardly from the tag strip,
   wherein the device comprises a pivot pin,
   wherein when the die assembly is in the stopped position and the die frame is moved in the first vertical direction, the die frame contacts respective contact surfaces of the first pincher and second pincher and drives the first pincher and second pincher to move in the two opposite rotational directions with respect to each other and about the pivot pin, and
   wherein the die frame comprises a first adjustor for setting a first position for the first pincher and a second adjustor for setting a second position for the second pincher, and wherein the first adjustor and the second adjustor each comprise a respective set screw for contacting the respective contact surfaces of the first pincher and second pincher.

2. The device of claim 1, wherein
   the first pincher comprises:
      a first main body portion,
      a first leg extending from the first main body portion, and
      a first receiving hole in the first main body portion; and
   the second pincher comprises:
      a second main body portion,
      a second leg extending from the second main body portion, and
      a second receiving hole in the second main body portion;
   wherein the first pincher and the second pincher are configured in mated relation to one another such that the first receiving hole and second receiving hole are aligned and the die assembly is U-shaped, and
   wherein the first pincher and the second pincher are secured to each other by the pivot pin extending through the first receiving hole of the first pincher and the second receiving hole of the second pincher.

3. The device of claim 2,
   wherein the die frame comprises a vertical slot through which the pivot pin extends and in which the pivot pin moves in the first vertical direction and the second vertical direction, wherein when the die assembly in is in a free position the die assembly is prevented from moving in the first vertical direction by the pivot pin contacting one end of the vertical slot, and
   wherein the pivot pin moves in the second vertical direction when the die assembly is in the stopped position and the die frame contacts respective contact surfaces of the first pincher and second pincher and drives the first pincher and second pincher to move in the two opposite rotational directions with respect to each other and about the pivot pin.

4. The device of claim 2, wherein the tag legs extending outwardly from the tag strip generally lie flat along a 0 degree reference plane, and wherein inner surfaces of the first leg and the second leg are each configured to engage and pivot the tag legs inwardly beyond 90 degrees from the 0 degree reference plane during operation of the device.

5. The device of claim 4, wherein the anvil comprises two undercuts on opposite side of the anvil into which opposite pairs of extending tag legs are bent inwardly beyond 90 degrees from the 0 degree reference plane during operation of the device.

6. The device of claim 1, wherein the die assembly comprises one or more stop contacting surfaces for contacting the die assembly stop when the die assembly is in the stopped position.

7. The device of claim 1, wherein the first pincher and the second pinchers each comprise a respective top surface comprising a contact surface and an angled surface.

8. The device of claim 1, wherein the device comprises:
   an actuator for moving the die frame in the first vertical direction and the second vertical direction,
   a handle assembly coupled to the actuator for moving the actuator to thereby move the die frame.

* * * * *